United States Patent
Gao et al.

(10) Patent No.: US 12,186,114 B2
(45) Date of Patent: Jan. 7, 2025

(54) DEEP RESIDUAL INCEPTION ENCODER-DECODER NETWORK FOR AMYLOID PET HARMONIZATION

(71) Applicants: Fei Gao, Sunnyvale, CA (US); Yi Su, Tempe, AZ (US); Jay Shah, Tempe, AZ (US); Teresa Wu, Tempe, AZ (US)

(72) Inventors: Fei Gao, Sunnyvale, CA (US); Yi Su, Tempe, AZ (US); Jay Shah, Tempe, AZ (US); Teresa Wu, Tempe, AZ (US)

(73) Assignees: ARIZONA BOARD OF REGENTS ON BEHALF OF ARIZONA STATE UNIVERSITY, Scottsdale, AZ (US); BANNER HEALTH, Phoenix, AZ (US)

( * ) Notice: Subject to any disclaimer, the term of this patent is extended or adjusted under 35 U.S.C. 154(b) by 0 days.

(21) Appl. No.: 18/659,581

(22) Filed: May 9, 2024

(65) Prior Publication Data
US 2024/0285244 A1     Aug. 29, 2024

Related U.S. Application Data

(63) Continuation of application No. PCT/US2022/051243, filed on Nov. 29, 2022.

(60) Provisional application No. 63/285,002, filed on Dec. 1, 2021.

(51) Int. Cl.
| | | |
|---|---|---|
| *A61B 6/03* | (2006.01) | |
| *G06T 5/20* | (2006.01) | |
| *G06T 15/00* | (2011.01) | |
| *H04N 19/117* | (2014.01) | |
| *H04N 19/176* | (2014.01) | |

(52) U.S. Cl.
CPC ............. *A61B 6/037* (2013.01); *G06T 5/20* (2013.01); *G06T 15/00* (2013.01); *H04N 19/117* (2014.11); *H04N 19/176* (2014.11)

(58) Field of Classification Search
USPC .................................................. 382/131
See application file for complete search history.

(56) References Cited

U.S. PATENT DOCUMENTS

| | | | | |
|---|---|---|---|---|
| 10,433,802 | B2 * | 10/2019 | Wenzel | A61B 6/5205 |
| 11,361,431 | B2 * | 6/2022 | Zaharchuk | A61B 6/5205 |
| 2016/0128660 | A1 | 5/2016 | Wenzel et al. | |
| 2017/0071562 | A1 * | 3/2017 | Suzuki | G06T 5/00 |
| 2020/0311914 | A1 * | 10/2020 | Zaharchuk | A61B 6/501 |
| 2021/0052233 | A1 * | 2/2021 | Kaplan | G16H 50/30 |

OTHER PUBLICATIONS

Xu et al., 200x Low dose PET Reconstruction using Deep Learning, arXiv:1712.04119v1 [cs.CV] Dec. 12, 2017, pp. 1-9. (Year: 2017).*

(Continued)

*Primary Examiner* — Ishrat I Sherali
(74) *Attorney, Agent, or Firm* — Snell & Wilmer L.L.P.

(57) ABSTRACT

Using deep learning, imaging harmonization among images produced with differing PET tracers is achieved. A method may include providing an original PET image of the brain using an original PET tracer, providing a target PET tracer, and converting, using a deep learning neural network, the original PET image into a target PET image simulating the image that would be obtained had the target PET tracer been used.

18 Claims, 4 Drawing Sheets

(56) References Cited

OTHER PUBLICATIONS

International Searching Authority, International Search Report and Written Opinion dated Mar. 6, 2023 in International Serial No. PCT/US2022/51243.

Liu et al. "Artificial intelligence-based image enhancement in pet imaging: Noise reduction and resolution enhancement." PET clinics 16.4 (2021): 553-576. Oct. 2021.

Klyuzhin et al. "Use of a tracer-specific deep artificial neural net to denoise dynamic PET images." IEEE transactions on medical imaging 39.2 (2019): 366-376. Jul. 5, 2019.

Chen et al. "18F-FDOPA PET imaging of brain tumors: comparison study with 18F-FDG PET and evaluation of diagnostic accuracy." Journal of Nuclear Medicine 47.6 (2006): 904-911. Jun. 2006.

Pinto et al. "Harmonization of brain diffusion MRI: Concepts and methods." Frontiers in Neuroscience 14 (2020): 396. May 6, 2020.

\* cited by examiner

DEEP RESIDUAL INCEPTION ENCODER-DECODER NETWORK FOR AMYLOID PET HARMONIZATION

CROSS-REFERENCE TO RELATED APPLICATIONS

This application is a continuation of PCT Application Serial No. PCT/US2022/051243 filed on Nov. 29, 2022, now WIPO publication WO 2023/101959 entitled "Deep Residual Inception Encoder-Decoder Network For Amyloid PET Harmonization." PCT/US2022/051243 claims priority to and the benefit of U.S. Provisional Patent Application No. 63/285,002 filed on Dec. 1, 2021, entitled "Deep Residual Inception Encoder-Decoder Network for Amyloid PET Harmonization." The disclosure of the foregoing applications is incorporated herein by reference in its entirety, including but not limited to those portions that specifically appear hereinafter, but except for any subject matter disclaimers or disavowals, and except to the extent that the incorporated material is inconsistent with the express disclosure herein, in which case the language in this disclosure shall control.

FEDERALLY SPONSORED RESEARCH OR DEVELOPMENT

This invention was made with government support under grant Nos. R01AG031581, R01AG069453, and P30AG019610 awarded by the National Institutes of Health. The government has certain rights in the invention.

TECHNICAL FIELD

The present disclosure relates to imaging, and in particular to techniques for imaging brain structure and activity.

BACKGROUND

Amyloid and tau are the defining pathologies of Alzheimer's disease (AD) and their abnormality initiates long before clinical symptoms onset. While postmortem neuropathological assessments are the gold standard for determining the existence and severity of these pathologies, the development of radio-labelled tracers allows the n vivo detection and quantification of amyloid and tau burdens using positron emission tomography (PET). Since the development of these PET tracers, they have been adopted in many research studies including the Alzheimer's Disease Neuroimaging Initiative (ADNI), the Dominantly Inherited Alzheimer's Network (DIAN) and others. It is determined that amyloid plaques can be detected at least 15 years prior to AD symptom onset and the prevalence of amyloid positivity increases with age from approximately 10% at age 50 to 44% at age 90 in cognitively normal populations. Imaging measurements of brain amyloid and tau pathology help to define AD in its preclinical stage and allow the investigation of the genesis and progression of AD. Many clinical trials have been designed to include amyloid and tau PET imaging for the assessment of treatment efficacy and target engagement as surrogate biomarkers. Human amyloid imaging started more than 15 years ago with the development of the [C11]-Pittsburgh compound (PIB), and has since been widely adopted by many research groups. Because of its short half-life (20 minutes), the use of PIB is limited to large research centers with access to onsite cyclotron and experienced radiochemistry teams. A number of F18 labeled amyloid tracers were later developed to address this limitation including florbetapir (FBP), florbetaben (FBB), flutemetamol (FTE), and NAV4694 (NAV), with the first three subsequently receiving FDA approval for amyloid imaging. With multiple PET tracers designed for the same target pathology, each tracer has its own target binding affinity, tracer kinetic behavior, non-specific binding, and tissue retention. Hence the imaging data acquired display tracer-dependent characteristics. Recent cross-sectional comparison studies demonstrated that the global amyloid burden measures derived from PIB and FBP have a shared variance ranging from approximately 70% to 90% depending on the quantification pipelines and cohorts. These tracers also show different levels of variability in the amyloid burden measurements. Inter-tracer variability leads to inconsistent amyloid positivity threshold and poses challenges for multi-center studies. A mean cortical FBP standard uptake value ratio (SUVR) cutoff of 1.17 was determined to detect moderate to frequent brain amyloid burden based on pathological assessment. This can be converted to a Centiloid cutoff of 37.1 CL using published equations. A recent study based on PIB imaging found a threshold of 20.1 CL to be optimal; and a FBB based study determined a threshold of 19 CL. The Centiloid approach was proposed to define a common numerical scale hoping to unify the global amyloid measures derived from different tracers and analysis pipelines. However, the amyloid measurements still have the same level of correlation between tracers, and the inherent signal to noise property also remains the same which is a main reason for the discrepancies in amyloid positivity cutoff aforementioned.

Differences in amyloid measurements across tracers also pose problems for longitudinal studies. The tracer difference results in different capabilities of tracking longitudinal amyloid accumulation which is especially important in clinical trials. In our recent study, we estimated that the sample size needed to detect a 20% reduction in the rate of amyloid accumulation was 305 per arm when PIB is used as the amyloid tracer while a sample size of 2156 is needed for FBP. Furthermore, strategies enabling the detection of focused changes and investigating the spatial patterns of pathological changes which require regional and voxel level details are currently lacking. One viable solution may be the emerging Artificial Intelligence technology: deep learning. Accordingly, improved systems and methods utilizing the same are desirable.

SUMMARY

In various embodiments, methods for image harmonization of a brain are disclosed. The method may include providing an original PET image of the brain using an original PET tracer, providing a target PET tracer, and converting, using a deep learning neural network, the original PET image into a target PET image simulating the image that would be obtained had the target PET tracer been used.

In various embodiments, the deep learning neural network may include a U-Net like architecture. The deep learning neural network may include at least one residual block. The deep learning neural network may include nine residual blocks. The at least one residual block may include one or more encoding blocks and one or more decoding blocks.

In various embodiments, each encoding block may receive a first input matrix, and each encoding block may include a first convolutional path which may include a first convolutional layer. The first convolutional layer may include a first kernel and a first filter bank. The first convolutional layer may receive the input matrix and may generate a matrix as an output. The first convolutional path may include a second convolutional layer. The second convolutional layer may include a second kernel and a second filter bank. The second convolutional layer may receive the output of the first convolutional layer as an input and may generate a matrix as an output. Each encoding block may include a second convolutional path which may include a third kernel. The second convolutional path may include a third filter bank and may generate a matrix as an output. Each encoding block may sum together the output of the first convolutional path and the output of the second convolutional path resulting in a first summed matrix. Each encoding block may down-sample the first summed matrix. Each encoding block may generate a matrix as an output.

In various embodiments, the first and second kernel may each include a 3 by 3 kernel. The third kernel may include a 1 by 1 kernel. The first, second, and third filter banks may each include a 32-channel filter bank. The first input matrix may include a 2D slice of an original PET image and may include a 256 by 256 matrix. The output of the first convolutional layer may include a 256 by 256 by 32 matrix. The output of the second convolutional layer may include a 256 by 256 by 32 matrix. The output of the second convolutional path may include a 256 by 256 by 32 matrix. The first summed matrix may include a 256 by 256 by 32 matrix. The first summed matrix may be down-sampled using a rectified linear unit (ReLu) function. The output of the encoding block may include a 128 by 128 by 32 matrix.

In various embodiments, each decoding block may receive a second input matrix from a corresponding encoding block and a third input matrix from another decoding block. Each decoding block may concatenate the second input matrix with the third input matrix to form a concatenated input matrix. Each decoding block may include a third convolutional path which may include a third convolutional layer. The third convolutional layer may include a fourth kernel and a fourth filter bank. The third convolutional layer may receive the concatenated input matrix and may generate a matrix as an output. The third convolutional path may include a fourth convolutional layer. The fourth convolutional layer may include a fifth kernel and a fifth filter bank. The fourth convolutional layer may receive the output of the third convolutional layer and may generate a matrix as an output. Each decoding block may include a fourth convolutional path which may include a sixth filter bank. The fourth convolutional path may receive the concatenated input matrix and may generate a matrix as an output. Each decoding block may include a sixth kernel. Each decoding block may sum together the output of the third convolutional path and the output of the fourth convolutional path resulting in a second summed matrix. Each decoding block may process the second summed matrix using the sixth kernel and may generate a matrix as an output.

In various embodiments, the fourth and fifth kernels may each include a 3 by 3 kernel. The sixth kernel may include a 1 by 1 kernel. The fourth, fifth, and sixth filter banks may each include a 32-channel filter bank. The second input matrix may include a 256 by 256 by 32 matrix. The third input matrix may include a 256 by 256 by 32 matrix. The concatenated input matrix may include a 256 by 256 by 64 matrix. The output of the third convolutional layer may include a 256 by 256 by 32 matrix. The output of the fourth convolutional layer may include a 256 by 256 by 32 matrix. The output of the fourth convolutional path may include a 256 by 256 by 32 matrix. The second summed matrix by include a 256 by 256 by 32 matrix. The output of the decoding block may include a 256 by 256 matrix and may include a 2D slice of the target PET image. The residual blocks may include five encoding blocks and four decoding blocks.

In various embodiments, the original PET tracer may include one of the [C11]-Pittsburgh compound (PIB), florbetapir (FBP), florbetaben (FBB), flutemetamol (FTE), and NAV4694 (NAV). The target PET tracer may include one of the [C11]-Pittsburgh compound (PIB), florbetapir (FBP), florbetaben (FBB), flutemetamol (FTE), and NAV4694 (NAV). The original PET image may include a two-dimensional image. The target PET image may include a two-dimensional image. The original PET image may have a size of 256 pixels by 256 pixels. The target PET image may have a size of 256 pixels by 256 pixels. The original PET image may include a three-dimensional image. The target PET image may include a three-dimensional image. The original PET image may be converted into a series of original two-dimensional images. Each original two-dimensional image may be converted into a target two-dimensional image. The target two-dimensional images may be recombined to form a target PET image. The series of original two-dimensional images may include coronal, sagittal, and axial views. The series of target two-dimensional images may include coronal, sagittal, and axial views.

The contents of this section are intended as a simplified introduction to the disclosure and are not intended to limit the scope of any claim. The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

With reference to the following description and accompanying drawings.

DETAILED DESCRIPTION

Figure 1:
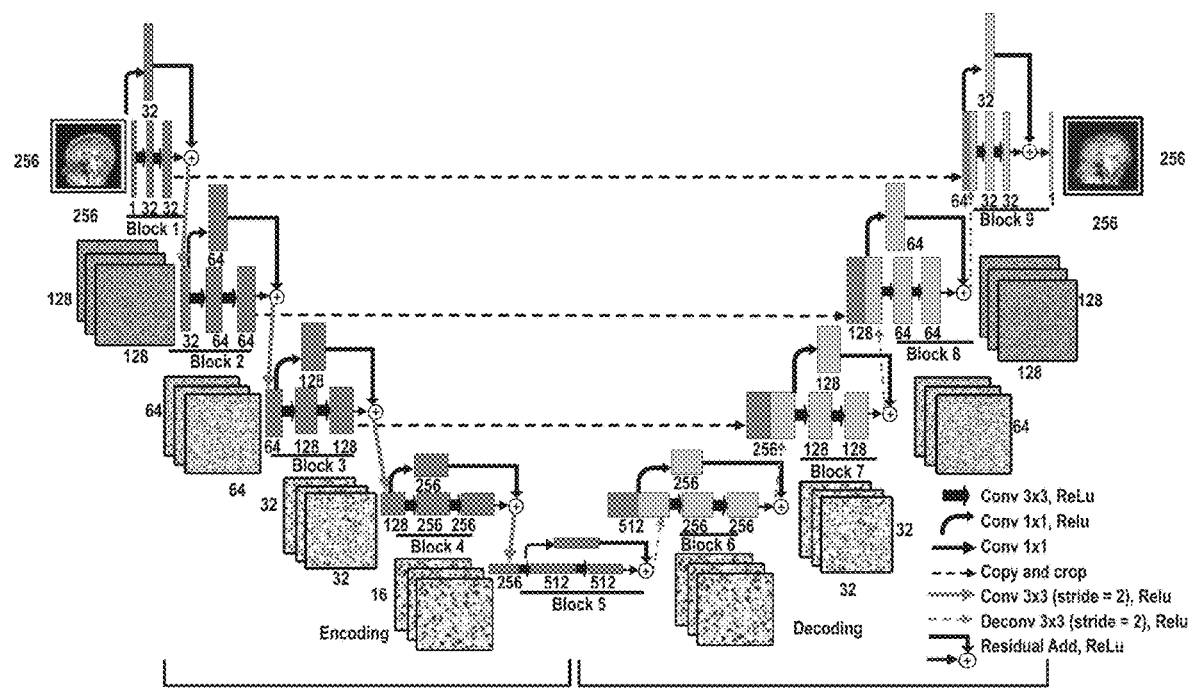
FIG. 1 illustrates the overall architecture of an exemplary residual inception encoder-decoder network (RIED-Net) in accordance with an exemplary embodiment.

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from principles of the present disclosure. For example, the steps recited in any of the method or process descriptions may be executed in any suitable order and are not necessarily limited to the order presented. Furthermore, any reference to singular includes plural embodiments, and any reference to more than one component or step may include a singular embodiment or step For the sake of brevity, conventional techniques and components for mathematical processes, transforms, mapping, smoothing, and/or the like may not be described in detail herein. Furthermore, the connecting lines shown in various figures contained herein are intended to represent exemplary functional relationships and/or physical couplings between various elements. It should be noted that many alternative or additional functional relationships or physical connections may be present in exemplary methods and systems for imaging and/or components thereof.

As used herein, "data." "information," or the like may include encompassing information such as commands, queries, files, messages, data for storage, and/or the like in digital or any other form.

As used herein, "satisfy," "meet." "match," "associated with," or similar phrases may include an identical match, a partial match, meeting certain criteria, matching a subset of data, a correlation, satisfying certain criteria, a correspondence, an association, an algorithmic relationship, and/or the like. Similarly, as used herein, "authenticate" or similar terms may include an exact authentication, a partial authentication, authenticating a subset of data, a correspondence, satisfying certain criteria, an association, an algorithmic relationship, and/or the like.

Methods are provided. In the detailed description herein, references to "various embodiments," "one embodiment," "an embodiment," "an example embodiment," etc. indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Amyloid and tau are the defining pathologies of Alzheimer's disease (AD) and their abnormality initiates long before clinical symptoms onset. Positron emission tomography (PET) makes it possible to detect and image brain amyloid and tau pathology for an individual in vivo. However, due to the differences in chemical properties between different PET tracers, including target binding affinity, tracer kinetic behavior, non-specific binding, and tissue retention, the PET images have an inconsistent amyloid positivity threshold and pose challenges for multi-center studies.

In particular, clinical trials include amyloid and tau PET imaging for the assessment of treatment efficiency and target engagement as surrogate biomarkers. The current amyloid and tau PET imaging methods with different PET tracers have a shared variance ranging from approximately 70% to 90% depending on the quantification pipelines and cohorts. To address these shortcomings of prior approaches, exemplary embodiments provide methods using deep learning to produce harmonization of images between different PET tracers.

With reference now to FIGS. 1, 2, 3, and 4, in accordance with an exemplary embodiment, exemplary methods utilize concepts from PET image processing and provide techniques related to image reconstruction, attenuation, and scatter correction. However, all practical applications of principles of the present disclosure are contemplated herein.

In an exemplary embodiment, in an image conversion method, a method comprises five encoding blocks and four decoding blocks, and comprises various convolution operations within each encoding block, and comprises various deconvolution operations within each decoding block, as illustrated in FIG. 1. This is an architecture similar to U-Net (Ronneburger et al., *U-net: Convolutional networks for biomedical image segmentation*. International Conference on Medical Image Computing and Computer-Assisted Intervention: Springer: 2015, p. 234-41; the entire contents of which are hereby incorporated by reference) and with the addition of a residual inception short-cut path that has been shown to improve training efficiency. Each block has a conventional convolution/deconvolution path with two 3 by 3 convolutional layers, and in parallel, a 1 by 1 convolution path. The output matrices from these two parallel paths are summed together and down/up sampled by a factor of 2 to serve as the input to the next block.

Figure 2:
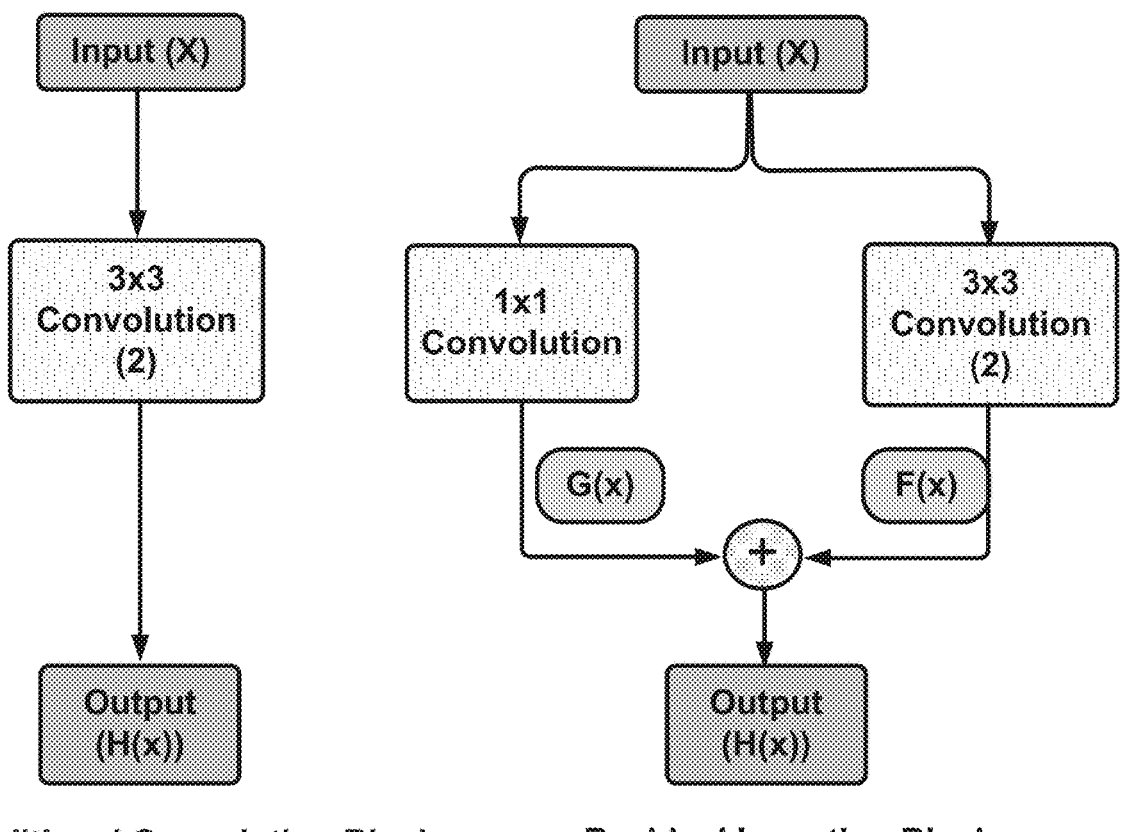
FIG. 2 illustrates a comparison between a traditional convolutional block in a U-Net and a residual inception block in an exemplary RIED-Net in accordance with an exemplary embodiment.

In an exemplary embodiment, in a convolution method, a method comprises learning the difference (F) between mapping and original input x, as illustrated in FIG. 2. Usually, a deep network (like a U-Net) estimates an output by learning a mapping function H, from input x to an output H(x). Instead of learning the direct mapping H, residual networks (like a RIED-Net) attempt to learn the difference (F) between mapping and original input x. A projection or estimation of x (labeled G(x)) can be used instead of direct input features. G(x) is generated using a simple [1×1] convolution to match the dimensions of the input. It is easier to learn the residual of output and input than the actual input, so the residual inception block is better than the traditional convolution block. Further, the use of residual blocks can address gradient vanishing issues from deep models.

Figure 3:
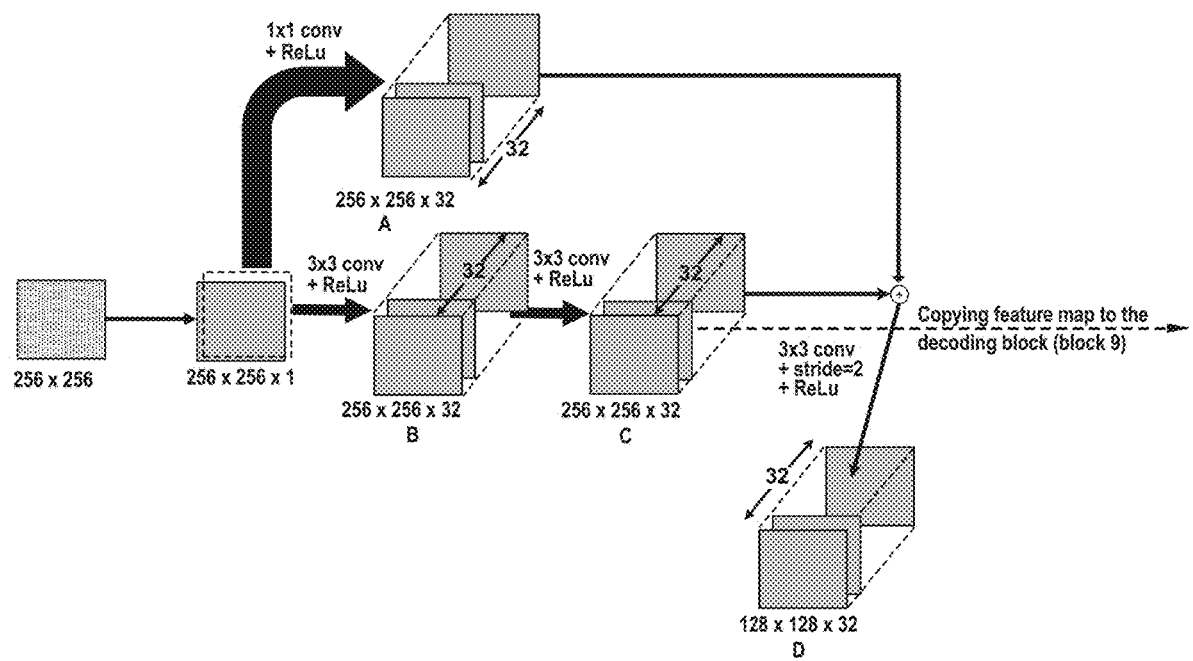
FIG. 3 illustrates details of an encoding block of an exemplary RIED-Net model using the first residue inception block as an example in accordance with various exemplary embodiments.

In an exemplary embodiment, as illustrated in FIG. 3, in one or more encoding blocks, the input can be a 2D slice of a PET image, for example as represented as a 256 by 256 matrix. The matrix can be processed in two parallel paths: a traditional convolutional path with two layers of 3 by 3 kernels and a separate convolutional path with one layer of a 1 by 1 kernel (function G in FIG. 2). The traditional convolution path comprises a first convolutional layer which uses a 32-channel filter bank and generates a 256 by 256 by 32 matrix (B) as an output. The traditional convolution path further comprises a second convolutional layer which receives matrix B an input and uses another 32-channel filter bank to generate another 256 by 256 by 32 matrix (C) as an output. The separate convolutional path uses a 32-channel 1 by 1 filter bank and generates another 256 by 256 by 32 matrix (A) as an output. Matrices A and C are summed together and then down-sampled by a factor of two using a rectified linear unit (ReLu) function (or other suitable function) to generate a 128 by 128 by 32 matrix (D). Matrix D serves as the input for the next encoding block. Matrix C serves as the partial input for the corresponding decoding block.

Figure 4:
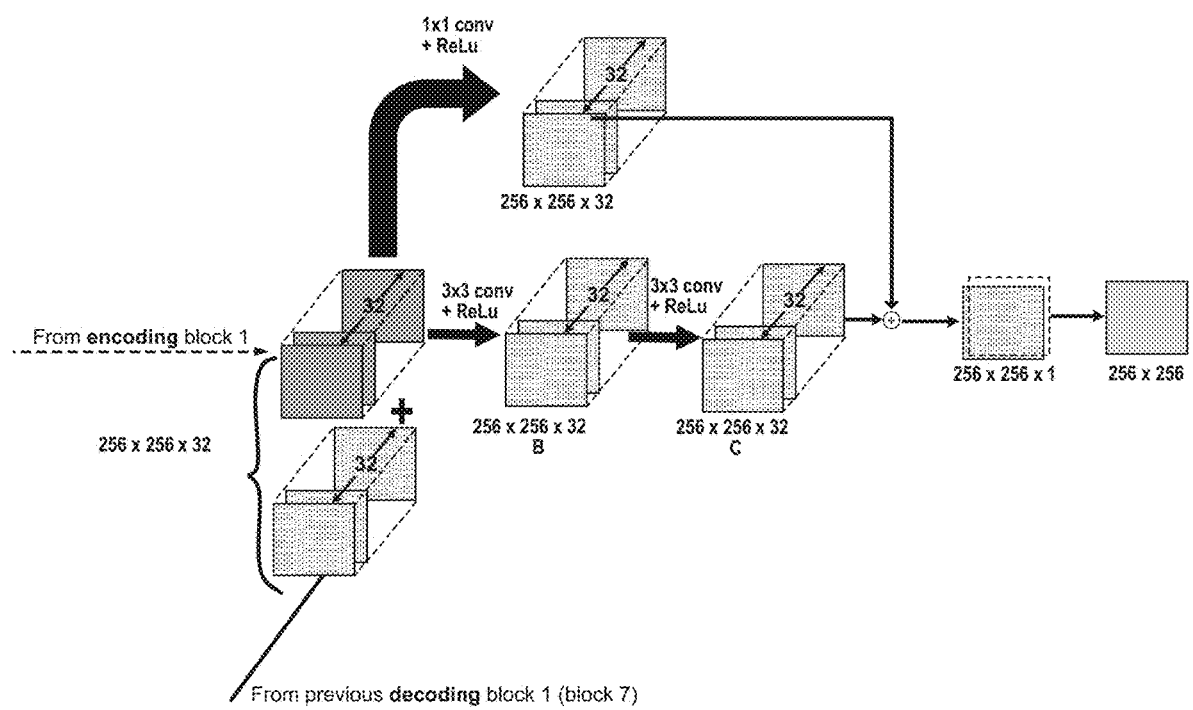
FIG. 4 illustrates details of a decoding block of an exemplary RIED-Net model using the last block as an example in accordance with various exemplary embodiments.

In an exemplary embodiment, as illustrated in FIG. 4, in one or more decoding blocks, the input can comprise a 256 by 256 by 32 output matrix from the corresponding encoding block and a 256 by 256 by 32 output matrix from the previous decoding block. These two matrices are concatenated into a 256 by 256 by 64 matrix. This input matrix can be processed in two parallel paths: a traditional convolutional path with two layers of 3 by 3 kernels and a separate convolutional path with one layer of a 1 by 1 kernel. The traditional convolution path comprises a first convolutional layer which uses a 32-channel filter bank and generates a 256 by 256 by 32 matrix (B) as an output. The traditional convolution path further comprises a second convolutional layer which receives matrix B an input and uses another 32-channel filter bank to generate another 256 by 256 by 32 matrix (C) as an output. The separate convolutional path uses a 32-channel 1 by 1 filter bank and generates another 256 by 256 by 32 matrix (A) as an output. Matrices A and C can be summed together and processed by a 1 by 1 convolutional kernel to generate a target 2D output image slice.

Via application of principles of the present disclosure, an exemplary RIED-Net model is able to harmonize amyloid PET images acquired using different tracers. Further, an exemplary RIED-Net model is able to improve the agreement in amyloid measures from two different tracers for both global indices and voxel-wise similarities. An exemplary RIED-Net model can be generalized to external imaging data and achieve favorable performance without additional tuning of the model. An exemplary RIED-Net model is robust to variabilities in imaging acquisition protocols and scanner differences when standard scanner harmonization protocols are implemented.

An exemplary RIED-Net model has two major advantages. First, RIED-Net focuses on voxel mapping instead of using patch-based approaches. Compared to an exemplary RIED-Net model, patch-based approaches sacrifice synthesis performance at the voxel levels. Second, an exemplary RIED-Net model is computationally affordable. This gives an exemplary RIED-Net model the potential to perform PET harmonization in 3D. Because an exemplary RIED-Net model is trained on each of the three orthogonal views of the input 3D images, RIED-Net avoids the unwanted noises across 2D slices that occur with other 2D models.

Working Example

Participants. From Open Access Series of Imaging Studies (OASIS), 92 participants aged 43-88 years were identified who had [C11]-Pittsburgh compound (PIB) and florbetapir (FBP) PET scans within 3 months. This dataset was used for training and cross-validation of the RIED-Net as a PET harmonization model. An independent dataset of 46 participants aged 21-89 years with paired PIB and FBP PET scans were downloaded from the Centiloid Project website and served as the external validation (GAAIN) set. All studies were approved by their corresponding institutional review board and written informed consent was obtained for each participant.

Imaging. For the OASIS dataset, dynamic PIB PET scan was acquired on a Siemens Biograph 40 PET/CT or a Siemens/CTI EXACT HR+ scanner for 60 minutes after tracer administration and reconstructed using standard iterative methods with attenuation and scatter correction. Dynamic FBP PET was acquired on a Siemens Biograph mMR scanner for 70 minutes after FBP administration and reconstructed using an ordered subset expectation maximization (OSEM) algorithm and attenuation/scatter corrected using a separately acquired low dose CT scan. For each participant, a T1-weighted MRI scan was also acquired using a 3T MR scanner. All imaging were acquired at the Washington University in St. Louis, and individual scans for each participant were completed within 3 months. The imaging acquisition information for the GAAIN dataset has been previously described in Navitsky et al., *Standardization of amyloid quantitation with florbetapir standardized uptake value ratios to the Centiloid scale*. Alzheimers Dement. 2018, the entire contents of which are hereby incorporated by reference. Briefly. PIB PET was acquired between 50-70 minutes post-injection, and FBP PET was acquired 50-60 minutes post-injection. The imaging pair was obtained an average of 18 days apart, and a 3T T1 MRI was obtained for each subject within 6 months of PET acquisition. One participant in the GAAIN cohort was excluded from further analysis due to poor quality of the T1 MRI.

The T1 weighted MRI data was analyzed using FreeSurfer (Martinos Center for Biomedical Imaging, Charlestown, Massachusetts, USA) to define anatomical regions. Amyloid PET imaging quantification was then performed using our standard protocols that included scanner harmonization, motion correction, target registration, and regional value extraction using a PET unified pipeline (PUP). The output included a standard uptake value ratio (SUVR) image using cerebellar cortex as the reference region and a mean cortical SUVR (MCSUVR) as the global index of brain amyloid burden. For the OASIS cohort, the PIB PET data were summed between 30-60 minutes and the FBP data were summed between 50-70 minutes post-injection to generate the SUVR images and the MCSUVR global indices. For the GAAIN cohort, the PIB and FPB PET data were summed between the 50-70 minutes and 50-60 minutes post-injection window for the quantification. The SUVR images were transformed in to the MNI152 template space via affine transformation established based on the T1 MRI image and served as the input to the RIED-Net model for training, internal validation, and external validation. All MCSUVR measurements were also converted to the Centiloid scale (CL) using pre-established equations and procedures to facilitate the cross-tracer comparison and interpretation.

Deep Learning Model for PET Harmonization. In an exemplary embodiment, we used 10-fold Cross-Validation (CV) in the training. Specifically, for the OASIS dataset, we shuffled the dataset randomly and created 10 different groups of the dataset, for an even split, we decided to use 90 out of 92 total samples (excluding the last two participants according to alphabetical order) and created 10 different folds of size 81:9 (total 90) where 81 was used for training and validation, and 9 was used for testing respectively. These folds are generated such that there is no overlap among the training and testing samples and the test dataset in each fold is always unique. We performed this 10-fold CV technique for all three views: coronal, sagittal and axial. For each view and fold, individual FBP 2D slices (256×256) from the 81 patients were used as the input, and the PIB 2D slices with respect to the same patients were taken as output to train and validate the RIED-Net model. Among the 2D slices obtained from 81 patients, we used a 90:10 split for training and internal validation. For each fold, we trained the model for a total of 40 epochs with batch-size of 16 (determined by the computing resource) and mean absolute error (MAE) as the loss function optimized by the model. We used Adam (Kingma et al., *A method for stochastic optimization*, arXiv preprint arXiv:14126980. 2014: the entire contents of which are hereby incorporated by reference) as the optimizer with a learning rate of 0.002 and a decay rate of 0.0005. For the other parameters we used default settings of the Keras platform. The validated model for that fold was then used to generate synthetic PIB SUVR images from FBP image for the remaining 9 patients serving as testing. Using the 10-fold CV procedure, synthetic PIB SUVR image was generated for each view and an average synthetic 3D PIB SUVR image was then generated combining the three views which was used as the main target for performance evaluation.

To obtain a single model from the OASIS dataset and test its performance on the independent GAAIN dataset to further evaluate the generalizability of an exemplary approach, we retrained the models using 80 out of the 92 OASIS samples that had the largest field of view (FOV) coverage and applied the models to generate synthetic PIB SUVR images for samples within the independent GAAIN dataset. Similar to the experiment on OASIS dataset only, synthetic PIB SUVR images for GAAIN dataset were generated for each view and the average 3D image across all three views was used as the main target for performance evaluation.

Additional principles of the present disclosure may be set forth in this publication: Shah J. Gao F. Li B, et al. Deep residual inception encoder-decoder network for amyloid PET harmonization. *Alzheimer's Dement.* 2022:1-10. Available at https://doi.org/10.1002/alz.12564 as of November 2022.) The disclosure of the foregoing is incorporated herein by reference in its entirety, including but not limited to those portions that specifically appear hereinafter, but except for any subject matter disclaimers or disavowals, and except to the extent that the incorporated material is inconsistent with the express disclosure herein, in which case the language in this disclosure shall control.

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling." or any other variation thereof, are intended to cover a physical connection, an electrical connection, a magnetic connection, an optical connection, a communicative connection, a functional connection, and/or any other connection. When language similar to "at least one of A, B, or C" or "at least one of A, B, and C" is used in the specification or claims, the phrase is intended to mean any of the following: (1) at least one of A: (2) at least one of B; (3) at least one of C; (4) at least one of A and at least one of B; (5) at least one of B and at least one of C; (6) at least one of A and at least one of C; or (7) at least one of A, at least one of B. and at least one of C.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises." "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. An image harmonization method for a brain, the method comprising:
    providing an original PET image of the brain using an original PET tracer;
    providing a target PET tracer; and
    converting, using a deep learning neural network, the original PET image into a target PET image simulating an image that would be obtained had the target PET tracer been used,
    wherein the deep learning neural network comprises a U-Net-like architecture,
    wherein the deep learning neural network comprises at least one residual block,
    wherein the at least one residual block comprises one or more encoding blocks and one or more decoding blocks, and
wherein each encoding block receives a first input matrix, and each encoding block comprises:
    a first convolutional path comprising:
        a first convolutional layer comprising a first kernel and a first filter bank, wherein the first convolutional layer receives the first input matrix and generates a first output matrix, and
        a second convolutional layer comprising a second kernel and a second filter bank, wherein the second convolutional layer receives the first output matrix as an input and generates a second output matrix; and
    a second convolutional path comprising a third kernel, wherein the second convolutional path comprises a third filter bank and generates a third output matrix,
    wherein each encoding block (i) sums together the second output matrix and the third output matrix resulting in a first summed matrix, (ii) down-samples the first summed matrix, and (iii) generates a fourth output matrix.

2. The method of claim 1, wherein:
    the first kernel comprises a 3 by 3 kernel;
    the second kernel comprises a 3 by 3 kernel;
    the third kernel comprises a 1 by 1 kernel;
    the first, second, and third filter banks each comprise a 32-channel filter bank;
    the first input matrix comprises a 2D slice of the original PET image and comprises a 256 by 256 matrix;
    the first output matrix comprises a 256 by 256 by 32 matrix;
    the second output matrix comprises a 256 by 256 by 32 matrix;
    the third output matrix comprises a 256 by 256 by 32 matrix;

the first summed matrix comprises a 256 by 256 by 32 matrix;

the first summed matrix is down-sampled using a rectified linear unit (ReLu) function; and the fourth output matrix comprises a 128 by 128 by 32 matrix.

3. The method of claim 1, wherein the at least one residual block comprises five encoding blocks and four decoding blocks.

4. The method of claim 1, wherein the original PET tracer comprises one of the [C11]-Pittsburgh compound (PIB), florbetapir (FBP), florbetaben (FBB), flutemetamol (FTE), or NAV4694 (NAV).

5. The method of claim 1, wherein the target PET tracer comprises one of the [C11]-Pittsburgh compound (PIB), florbetapir (FBP), florbetaben (FBB), flutemetamol (FTE), or NAV4694 (NAV).

6. The method of claim 1, wherein the original PET image comprises a two-dimensional image.

7. The method of claim 1, wherein the target PET image comprises a two-dimensional image.

8. The method of claim 6, wherein the original PET image has a size of 256 pixels by 256 pixels.

9. The method of claim 7, wherein the target PET image has a size of 256 pixels by 256 pixels.

10. The method of claim 1, wherein the original PET image comprises a three-dimensional image.

11. The method of claim 1, wherein the target PET image comprises a three-dimensional image.

12. The method of claim 10, wherein the original PET image is converted into a series of original two-dimensional images, each original two-dimensional image being converted into a target two-dimensional image, and the target two-dimensional images are recombined to form the target PET image.

13. The method of claim 12, wherein the series of original two-dimensional images and the target two-dimensional images each comprise coronal, sagittal, and axial views.

14. An image harmonization method for a brain, the method comprising:

providing an original PET image of the brain using an original PET tracer;

providing a target PET tracer; and converting, using a deep learning neural network, the original PET image into a target PET image simulating an image that would be obtained had the target PET tracer been used, wherein the deep learning neural network comprises a U-Net-like architecture, wherein the deep learning neural network comprises at least one residual block, wherein the at least one residual block comprises one or more encoding blocks and one or more decoding blocks, and wherein each decoding block receives a second input matrix from a corresponding encoding block and a third input matrix from another decoding block, concatenates the second input matrix with the third input matrix to form a concatenated input matrix, each decoding block comprising:

a third convolutional path comprising:

a third convolutional layer comprising a fourth kernel and a fourth filter bank, wherein the third convolutional layer receives the concatenated input matrix and generates a fifth output matrix, and a fourth convolutional layer comprising a fifth kernel and a fifth filter bank, wherein the fourth convolutional layer receives the fifth output matrix and generates a sixth output matrix;

a fourth convolutional path comprising a sixth filter bank, wherein the fourth convolutional path receives the concatenated input matrix and generates a seventh output matrix; and a sixth kernel, wherein each decoding block (i) sums together the sixth output matrix and the seventh output matrix resulting in a second summed matrix, (ii) processes the second summed matrix using the sixth kernel, and (iii) generates an eighth output matrix.

15. The method of claim 14, wherein:

the fourth kernel comprises a 3 by 3 kernel;

the fifth kernel comprises a 3 by 3 kernel;

the sixth kernel comprises a 1 by 1 kernel;

the fourth, fifth, and sixth filter banks each comprise a 32-channel filter bank;

the second input matrix comprises a 256 by 256 by 32 matrix;

the third input matrix comprises a 256 by 256 by 32 matrix;

the concatenated input matrix comprises a 256 by 256 by 64 matrix;

the fifth output matrix comprises a 256 by 256 by 32 matrix;

the sixth output matrix comprises a 256 by 256 by 32 matrix;

the seventh output matrix comprises a 256 by 256 by 32 matrix;

the second summed matrix comprises 256 by 256 by 32 matrix; and the eighth output matrix comprises a 256 by 256 matrix and comprises a 2D slice of the target PET image.

16. The method of claim 14, wherein the at least one residual block comprises five encoding blocks and four decoding blocks.

17. The method of claim 14, wherein the original PET tracer comprises one of the [C11]-Pittsburgh compound (PIB), florbetapir (FBP), florbetaben (FBB), flutemetamol (FTE), or NAV4694 (NAV).

18. The method of claim 14, wherein the target PET tracer comprises one of the [C11]-Pittsburgh compound (PIB), florbetapir (FBP), florbetaben (FBB), flutemetamol (FTE), or NAV4694 (NAV).

* * * * *